United States Patent [19]

Hammer

[11] Patent Number: 4,939,464
[45] Date of Patent: Jul. 3, 1990

[54] NMR-PET SCANNER APPARATUS

[75] Inventor: Bruce E. Hammer, Latham, N.Y.

[73] Assignee: Intermagnetics General Corporation, Guilderland, N.Y.

[21] Appl. No.: 378,396

[22] Filed: Jul. 11, 1989

[51] Int. Cl.$^5$ ............................................. G01R 33/20
[52] U.S. Cl. ................................ 324/318; 128/653 R; 250/363.03; 250/368
[58] Field of Search ........................ 324/300, 307, 318; 250/363.03, 368; 128/653 R, 653 SC

[56] References Cited

FOREIGN PATENT DOCUMENTS 105982  6/1985  Japan ............................. 250/363.03

Primary Examiner—Michael J. Tokar
Assistant Examiner—Kevin D. O'Shea
Attorney, Agent, or Firm—Helfgott & Karas

[57] ABSTRACT

NMR-PET scanner apparatus is provided wherein a PET detector is disposed within a magnetic imaging structure of an NMR device. The output of the PET detector is conveyed through light pipes to photodetectors which are shielded and disposed without the magnetic imaging structure of the NMR device to avoid interaction between the photodetectors and the magnetic field generated by the magnetic imaging structure of the NMR device.

12 Claims, 3 Drawing Sheets

NMR-PET SCANNER APPARATUS

BACKGROUND OF THE INVENTION

This invention relates to Nuclear Magnetic Resonance (NMR) and Positron Emission Tomography(PET) scanner apparatus and more particularly, to scanner apparatus for performing both NMR and PET scanning and yielding improved spatial resolution of a PET image by achieving PET scanning in a magnetic field. The magnetic field is preferably made available by virtue of the NMR apparatus associated with the combined scanner.

The NMR phenomenon, which is now well known, can be employed to map tissue structure and measure biochemical pathways of compounds labelled with NMR active nuclei. For example, such techniques may be utilized to measure the metabolic pathway of C-13 enriched glucose in tissue. Other applications such as the detection of cancerous cells, as well as neurological applications, are well known.

The NMR phenomenon can be detected in materials that have isotopes with a net nuclear spin i.e., H-1, H-2, C-13, P-31, F-19. Thus, in the presence of an externally applied magnetic field the energy levels of these nuclei are no longer degenerate. Radiofrequency pulses are typically employed to stimulate transitions between energy levels. The nuclei that have a spin of one half have only two nuclear energy levels. Thermodynamics imposes a larger spin population for the lower energy state relative to the higher energy state. When the spin states are in thermal equilibrium, the population ratio between the upper and lower energy states is defined by Boltzman's equation $$N^+/N^- = \text{EXP}\,(-\Delta E/kT)$$

where:
$N^+$, $N^-$ = population upper and lower energy states, respectively
$\Delta E$ = energy difference between spin states (J)
k = Boltzman's constant (J/°K.)
T = spin temperature (°K.)

An RF pulse is generally utilized to stimulate transitions between energy levels. The frequency of radiation necessary to induce these transitions is defined by the Larmor equarion:

$$w = \gamma B$$

where:
w = frequency (rad/s)
$\gamma$ = gyromagnetic ratio (rad/T-s)
B = magnetic field (T)

Due to the excess spin population in the lower energy levels, more spins are transferred to the upper energy state than to the lower energy state during the presence of an RF pulse. Thus, the sample has a net absorption of RF energy. Due to molecular motions in the sample, spins in the higher energy levels are stimulated to transition to the lower energy levels and this process leads to the re-emission of absorbed RF energy which may typically be detected with a small signal amplifier. Spatial information can be obtained when time varying magnetic field gradients are employed during an NMR experiment. Chemical information naturally arises from the detected NMR signal because different configurations and conformations of molecules containing NMR active nuclei give rise to a range of NMR frequencies.

NMR imaging and spectroscopy has been applied to a number of medical and non-medical applications. In biological systems, the most commonly studied nucleus is the proton. This is because protons are the most abundant nuclei in tissue, possess the highest NMR sensitivity of any other nucleus with the exception of tritium, and have favorable spin-lattice and spin-spin relaxation times. Images of other nuclei in biological systems have been made, i.e., C-13, Na-23, P-31. These images are typically characterized by smaller gyromagnetic ratios, unfavorable relaxation times and metabolite concentrations being 1000 times smaller than water concentrations. Thus, the spatial resolution of images acquired from such nuclei are typically courser because of signal-to-noise and gradient strength considerations.

Tissue chemistry can also be studied by NMR spectroscopic techniques. Spatial localization of NMR spectra is possible for the more abundant nuclei such as H-1 and P-31. However, spatial localization of labelled metabolites such as C-13 enriched glucose and its C-13 labelled metabolic intermediates is possible but more difficult. This is especially so if C-13 labelled metabolites are in tissues which cannot be accessed by surface coils such as tissues deep within the brain. Thus, localized NMR spectroscopy of tagged molecules is difficult because of low signal to noise ratios. If an NMR labelled molecule could also be tagged with a positron emitter, i.e., C-11, a PET image would show the site of metabolism.

PET measures the spatial distribution of positron emitting radionuclides in an object. This is done by detecting annihilation photons from compounds labelled with positron emitting isotopes. Positrons are emitted from isotopes that have a low neutron to proton ratio or conversely, a high proton to neutron ratio. Thus, in order to achieve nuclear stability, a proton decays into a neutron, positron, and neutrino according to the formula:

$$^1_1H \rightarrow \beta^+ + {}^1_0n + \nu$$

where:
$^1_1H$ = proton
$\beta+$ = *positron*
$^1_0n$ = neutron
$\nu$ = neutrino Positrons hava a continuum of energies ranging from 0 MeV to $E_{max}$, where $E_{max}$ can correspond to a few MeV. Each positron emitting radionuclide has a unique distribution of positron energies. An emitted positron gradually loses its kinetic energy as it travels through matter. This kinetic energy is degraded by ionization and excitation interactions with orbital electrons of the atoms the positron passes. When a positron has lost most of its energy, it will combine with an electron to form a metastable positronium atom before the positron and electron mutually annihilate one another. As a result of the annihilation, the mass of the electron and positron are transformed into two 0.511 MeV photons which are emitted and travel in opposite directions.

It is precisely this radiation that a PET scanner is designed to detect. Thus, coincident detection of annihilation photons by a pair of radiation detectors, 180° apart, places the photons on a line through the sample. Time of flight measurements may be employed to localize the event to a small portion of the line.

However, resolution of a PET image is determined by extrinsic and intrinsic factors. Collimation, efficiency, and time resolution of the radiation detector provides the extrinsic limit of resolution which is approximately 1-2 mm. The distance a positron travels through matter before annihilation limits the intrinsic resolution of PET. While improvements in detector design and computer algorithms can usually improve the extrinsic resolution limit, the intrinsic resolution limit of PET imaging is generally only variable by utilizing radioisotopes having different positron energies. The smaller the position energy, the less a positron needs to travel before annihilation occurs and this will result in higher resolution. However, the method of employing radioisotopes having different positron energies is generally of limited use if compounds need to be labelled with specific positron emitting nuclides. A major weakness of PET is that it cannot depict tissue morphology or the metabolic fate of the labelled compound.

It has been determined that merging NMR and PET techniques into one device simultaneously enhances the strengths of each technique while minimizing their respective limitations. For example, H-1 NMR images provide structural information on the region of interest that PET is scanning. Further, NMR spectra of isotopically enriched metabolites, i.e. C-13, F-19, would delineate biochemical pathways. PET images of metabolites labelled for NMR studies and also tagged with a positron emitter would show the location of regional metabolism. In addition, in-plane resolution of PET images would be enhanced in a magnetic field. See for example, *A Simulation Study of a Method to Reduce Positron Annihilation Spread Distribution Using a Strong Magnetic Field in Positron Emission Tomography*, H. Iida, I. Kanno, S. Miura, M. Murakami, K. Takahashi, and K. Uemura, *IEEE Transactions on Nuclear Science*, Vol. 33, 1, Feb. 1986, pp. 597–600. Thus, while this article indicates at page 599, that the required magnetic field to reduce the spread of positron annihilation is terribly high, for practical PEt devices it has been determined that the field strengths available in NMR devices are appropriate to achieve a marked reduction in the spread of positron annihilations and to significantly improve the resolution of PET scanner according to the present invention.

The combination of NMR and PET scanning techniques within a scanner device, while providing theoretical enhancements of each techhique, imposes design constrains which are extremely onerous and might be considered to mandate the mutual exclusivity of each approach. More particularly, PET scanners normally employ photomultiplier tubes as part of their photon detection instrumentation. Photomultiplier tubes, in turn, do not function very well in magnetic fields and conversely, the magnetic field homogeneity which is mandatory in NMR operation is distored by ferromagnetic PMT assemblies. It has been determined that these problems may be overcome by coupling scintillation crystals to a rack of photomultiplier tubes through quartz light pipes and magnetically shielding the photomultiplier tube assembly once the same is located a suitable distance from the magnet. However some loss in efficiency of photon detection will occur with this approach. Alternatively ceramic or similar other detection crystals can be coupled to a photodiode. This eliminates the shielding requirements imposed upon systems designed with photomultipliers. Similarly superconducting colloidal detectors could also be used, here a photomultiplier tube is not required. These devices depend upon having a magnetic field for their operation. This field may be supplied by the NMR imaging magnet.

Therefore, it is a principal object of the instant invention to provide combined NMR-PET scanner apparatus. Various other objects and advantages of the present invention shall become clear from the following detailed description of an exemplary embodiment thereof and the novel features will be particularly pointed out in conjunction with the claims appended hereto.

SUMMARY OF THE INVENTION

In accordance with the teachings of the present invention, NMR-PET scanner apparatus is provided wherein a PET detector is disposed within the magnetic imaging structure of an NMR device and the output of the PET detector is conveyed through light pipe means to photodetector means which is shielded and disposed without the magnetic imaging structure of the NMR device to avoid interaction between the photodetector means and the magnetic field generated by the magnetic imaging structure of the NMR device.

BRIEF DESCRIPTION OF THE DRAWINGS

The invention will be more clearly understood by reference to the following detailed description of an exemplary embodiment thereof in conjunction with the accompanying drawings in which.

DETAILED DESCRIPTION

Figure 1:
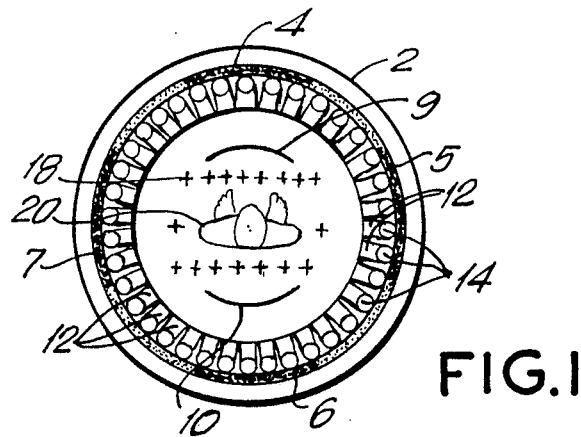
FIG. 1 is a cross-sectional view of a preferred embodiment of the NMR-PET scanner apparatus in accordance with the teachings of the present invention.

Referring now to the drawings and more particularly to FIG. 1 thereof, there is shown a cross-sectional view of a preferred embodiment of NMR-PET scanner apparatus in accordance with the teachings of the present invention. A side view of the scanner apparatus is illustrated in FIG. 2 and both FIGS. 1 and 2 should be consulted as this description proceeds.

Figure 2:
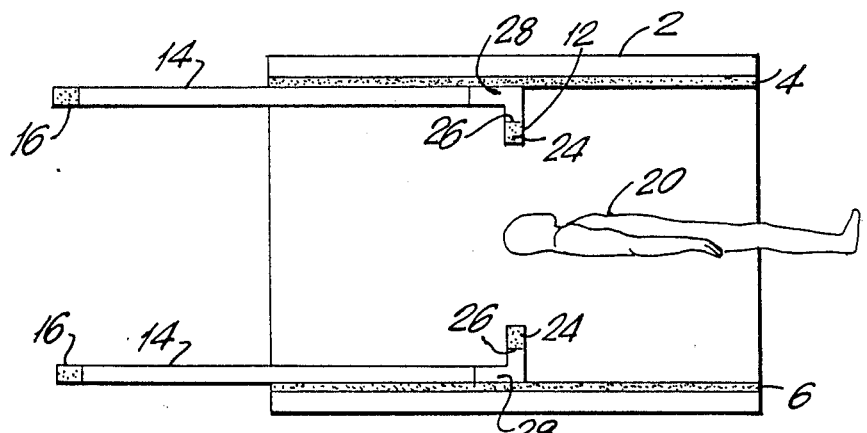
FIG. 2 is a side view, partially in section, of the preferred embodiment of the NMR-PET scanner apparatus shown in FIG. 1.

The preferred embodiment of the NMR-PET scanner apparatus depicted in FIGS. 1 and 2 comprises conventional magnetic imaging structure of an NMR device such as a superconducting magnet 2, gradient coils 4–7, and RF probe structure 9 and 10. In addition, a PET detector means 12 is provided at a location where PET scanning is to take place and the output of the PET detector means 12 is conveyed through light pipe means 14, to photodetector means 16.

The superconducting magnet 2, the gradient coils 4–7, and the RF probe structure 9 and 10 may comprise conventional magnetic imaging structure such as typically employed in NMR devices as well-known to those of ordinary skill in the art. The function of the superconducting magnetic 2 is to provide a uniform and stable externally applied magnetic field so that the nuclei to be examined no longer have degenerate energy levels. Thus, as well known to those of ordinary skill in the art, a superconducting magnetic 2 may be formed by a plurality of superconducting magnets arranged in the tube like structure illustrated in FIGS. 1 and 2 having a specific orientation and maintained at an appropriate temperature by mounting within a cryostat. Alternatively, should it be desired to employ a uniform steady magnetic field with less fringing, conventional magnetics may be employed. The uniform field generated by the superconducting magnet 2 is in the axial direction of the cylindrical superconducting magnet 2 is illustrated by the crosses 18 in FIG. 1 showing the same directed into the plane of the paper.

Similarly, the gradient coils 4–7 are in all ways conventional and are employed either in the usual manner to provide a select orientation to the field and/or alternattively for gradient sequence techniques wherein selected sequences of pulses and/or sinusoids are applied to the gradient coil to cause frequency and/or phase encoding of the distributed rotation of nuclear spin in the sample. The gradient coils 4–7 may take the conventional form of a wound coil arrangement, wherein the winding is again wound i the axial direction of the cylindrical structure formed so that the same may be selectively utilized to orient the applied magnetic field externally imposed on the subject 20 generally indicated in FIGS. 1 and 2. In this regard additional reference may be made for example to the article entitled *Magnetic Field Profiling: Analysis and Correcting Coil Design*, by F. Romeo and D. I. Hoult, Magnetic Resonance in Medicine, Vol. 1, pp. 44–65, 1984 and the references cited therein.

In like manner, the RF probe structure 9 and 10 may take the conventional form of an RF and sensing coil applied either to a portion of the subject 20 to be examined or disposed within the magnetic imaging structure of the NMR device where tissue within such structure is to be scanned. Those of ordinary skill in the art will appreciate that short duration RF pulses are introduced to stimulate transitions between energy levels in the nuclei being examined and thereafter the sensing coil associated therewith is employed to sense transitions in the nuclei when the same relax or return to a lower level energy state. Thus, an RF pulse is typically employed to stimulate transitions between energy levels while the sensing coil is utilized to detect a relaxation in the state of the energy level when the RF pulse terminates. This too is well known to those of ordinary skill in the art of NMR magnetic imaging.

The PET detector means 12 may take the conventional form of a scintillator crystal ring formed of individual 2"×2" NaI (Tl) crystals such as available from Harshaw/Filtrol Corporation of Solon, Ohio. Alternatively, BeGO crystals may be employed. The PET detector means 12 may be formed by as few as 64 2×2 crystals. However, higher resolution devices would require rings formed of 128, 256, 512, etc. crystals. While the instant PET detector means 12 is formed on a custom-made basis, it should be noted that a similar scintillation ring detector employing 64NaI (Tl) crystals, here 2 cm by 1.5 inch, has been fabricated and employed in a circular ring transverse axial positron camera as reported in the article entitled "*A Circular Ring Transverse Axial Positron Camera*" in an article entitled "*Reconstruction Chromography in Diagnostic Radiology and Nuclear Medicine*" by Chou, Erickson, and Chin, Ed. mm, proceedings University Park Press, Baltimore 1977 at pages 398 and 399. Similarly, scintillation crystals made from other inorganic salts or oxides such as BeGO (Beryllium-Germanium-Oxide) or plastics or ceramics could also be employed as well as superconducting colloidal detectors. In addition scintillator crystals can be designed so that angle type pointing logic is used. Since PET detectors made from these materials are non-conductive and non-ferromagnetic, their interaction with the magnetic fields generated by the superconducting magnet 2, the magnetic gradient coils 4–7, and the RF fields periodically present in the RF probe structure 9 and 10 will be minimal.

The PET detector means 12 in the form of a scintillator ring will generate in the well known manner a flash of light as a result of the presence of an ionizing particle or photon. Hence, should positron annihilation occur within the ring of the PET detector means 12, the two, 0.511 MeV photons emitted 180° apart as a result thereof will be detected by individual ones of the scintillation crystals making up the PET detector means 12.

Figure 3:
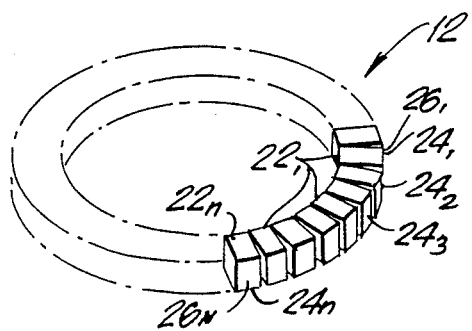
FIG. 3 is a diagram illustrating the details of a PET detector ring in accordance with the teachings of the present invention.

The individual 2"×2" sodium iodide (NaI(Tl)) crystals may be formed into a scintillator ring in the manner generally indicated in FIG. 3 which shows the details of an exemplary PET detector ring 12 in accordance with the teachings of the present invention. More particularly, referring to FIG. 3, it will be seen that each of the 2"×2" sodium iodide scintiallor crystals are formed into a ring shape by butting the faces $22_1$–$22_n$ of each sodium iodide crystal $24_1$–$24_n$ so that essentially a closed interior ring of crystals is formed. The edge portions adjacent to each face 22 typically may be physically mounted to the adjacent edge of the next crystal through the use of a suitable epoxy and light shield. The ring structure can contain multiple rings of scintillator crystals and depending on the preferred imaging technique can remain stationary, rotate, rotate-translate or wobble-rotate. Mechanisms used in moving the ring should be fabricated from non-magnetic and preferably non-conductive material. Filler material may be employed to the rear of each crystal or as shall be seen below, intermediate the light pipe means 14 to ensure that a rigid ring-like structure is formed. Obviously the epoxy material should be non-conductive and non-magnetic so as not to interfere or perturb the magnetic field in any manner.

Figure 4:
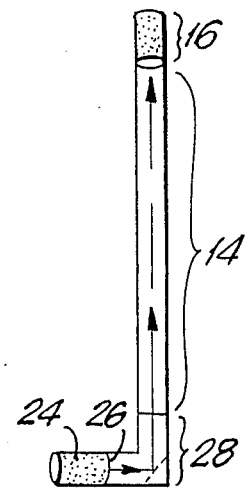
FIG. 4 is a diagram illustrating the details of an individual scintillator crystal within the PET detector ring illustrated in FIG. 3 showing the manner in which a light pipe and photodetector device is connected thereto.

Affixed to the end of each sodium iodide scintillation crystal 24 is a right angle quartz prism 28. The right angle quartz prism is best shown in FIG. 1 and 4. FIG. 4 shows the details of an individual scintillator crytal 24 within the PET detector ring illustrated in FIG. 3 illustrating the manner in which a light pipe 14 and photodetector means 16 is connected thereto. Thus as shown in FIG. 4, attached to the right angle quartz prism 28 is a light pipe 14 which acts, as shall be apparent to those of ordinary skill in the art, to convey flashes of light produced by the crystal 24 in response to a photon to a photodetector means 16. The right angle quartz prism acts in a manner well known to those of ordinary skill in the art to convey information generated by the scintillation crystal 24 into the light pipe 14. The right angle quartz prism is available from Harshaw/Filtro Company of Solon, Ohio.

The light pipe 14 as best illustrated in FIGS. 1 and 4 preferably takes the form of a 2 inch diameter acrylic cast rod whose length approximately corresponds to the axial length of the cylinder formed by the superconducting magnet 2. Since, as illustrated in FIG. 2, the PET detector means 12 is disposed approximately midway along the axial length of the cylindrical superconducting magnet 2, where the same may overly a subjects head, the light pipe means 14 extends substantially beyond the end portion of the superconducting magnet 2 to a location where the fringing fields associated therewith are sharply attenuated. While an acrylic cast rod is preferred for the light pipe means 14, optical fibers may also be employed for purposes of conveying the output of the scintillation crystal 24 to the photodetector means 16.

The photodetector means 16 is attached to each light pipe in the manner best illustrated in FIG. 4. The photodector means may take the form of a 2 inch photomultiplier tube with magnetic shielding such as available from EMI as a Model No. 9257 or alternatively a photoresponsive diode may be employed. In either case, the photodetector means, 16 would be be magnetically shielded by employing MU metal or soft iron in a manner well known to those of ordinary skill in the art. The number of photodetector means 16 would correspond to the number of scintillator crystals 24, the number of right angle quartz prisms 28, and the number of light pipe means 14. Hence, again as few as 64 crystals may be employed while higher resolution devices require more crystals, i.e., 128, 256, 512, etc.

The combination of extending the photodetector means 16 away from the fringing fields of the superconducting magnet 2 through the use of the light pipe means 14 together with the shielding of the photodetector means sharply reduces adverse interaction between the photodetector means 16 and the magnetic fields generated by the magnetic imaging structure of the NMR device. This, however, occurs at a cost of a decrease in photon detection sensitivity.

Through the use of light pipe means 14 to remove the ferromagnetic materials associated with the photodetector assembly 16 away from the fringing fields of the superconducting magnet 2, the photodetector means 16 will be able to properly function and the magnetic fields generated by the NMR device will not be subtantially perturbed. However, use of the right angle quartz prism 28, and disposing the photodetector means 16 away from the scintillation crystals 24 will result in a decrease in photodectection sensitivity on an order of 50%. In this regard, when scintillator crystals in the form of sodium iodide, beryllium-germanium-oxide, ceramic or plastic are employed, the right angle quartz prism 28 and the light pipe means 14 should be matched to the characteristics of the scintillation crystal. Furthermore, the length of the light pipe means 14 and the amount of shielding employed for the photodetector means 16 should be optimized for the nature of the fields imposed by the NMR imaging structure.

The intrinsic spatial resolution in PET imaging is limited by the distance a positron travels through matter. Typically the angle of ejection of a positron from a radionuclide can be considered isotropic. This means that if a sphere were drawn around a point source of positron emitting isotopes, an equal number of positrons per unit area could be measured over all a locations on the sphere's surface. The maximum distance that a positron can travel in matter is related to density and positron energy. A first order approximation of positron range in matter can be estimated by the equation:

$$D = (412 E^{1.265 - 0.09541 \ln E})/\rho$$

where
  D = range of positron (cm)
  E = positron energy (MeV)
  $\rho$ = density (g/cm$^3$)

See *Introduction to Health Physics*, by Herman Cember, p. 99 EQN: 52,2nd Ed. Pergamon Press Elmsford, N.Y. (1983)

D is the linear range a positron travels. However since its path through matter is tortuous, the actual radial distance travelled from the point of emission should be smaller. This simplistic model appears to be valid when the results are compared to Monte Carlo simulation of positron-matter interactions in a magnetic field. See *A simulation Study of a Method to Reduce Positron Annihilation Spread Distribution Using a Strong Magnetic Field in Positron Emission Tomography, supra.*

For purposes of illustration, monoenergetic positrons are considered. This means that all annihilation will be confined to regions inside a sphere bounded having a radius of r determined by the above equation. The probability distribution of annihilation within the sphere will be radially symmetric.

To simplify this discussion, it may be assumed that all annihilation events occur at the surface of the sphere. A charged particle moving through a magnetic field can have its trajectory changed according to the formula that:

$$\vec{F} = q\vec{V} X \vec{B}$$

where
  F = the force
  q = the charge
  V = the velocity vector, and
  B = the flux vector
while
  X corresponds to the cross product Since a cross product is involved it will immediately be appreciated that if the velocity of the charged particle is collinear with the magnetic field lines, no effect on trajectory of the charged particle occurs. However, if there is a component of velocity not aligned with the field direction, the charged particles would precess about the magnetic lines of flux in a spiral trajectory. If the charged particle travels in a plane perpendicular to the magnetic field, the particle should execute a circular orbit. The radius of such an orbit can be computed from the equation that:

$$r = mV/qB$$

where
  r = radius,
  m = the mass
  V = the velocity
  q = the charge, and

B is the magnetic field.

Figure 5:
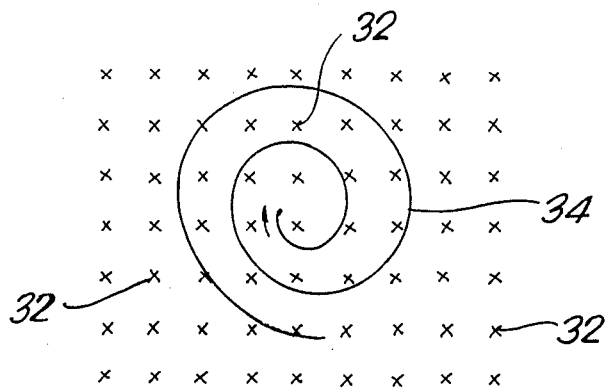
FIG. 5 is a diagram illustrating the effect on positron trajectory when a positron enters a magnetic field transverse to the flux lines.

Due to energy loss mechanisms the charged particle will not maintain a circular orbit but will spiral toward the center of the orbit. This is illustrated in FIG. 5 which is a diagram illustrating the effect on positron trajectory when a positron enters a magnetic field transverse to the flux lines. In FIG. 5 the crosses 32 indicate a magnetic field directed into the page while the helical path 34 illustrates the trajectory of a positron $\beta+$ entering perpendicular to the field 32. What results is that in the presence of a magnetic field positrons emitted transverse or perpendicular to the magnetic field will be confined to a range r as defined above assuming positron annihilation occurs at the spiral center.

Thus, in summary the distance that a positron can travel in a plane normal to the direction of magnetic flux is less than or equal to the positron range of a positron that has a velocity component parallel to the magnetic flux lines. This means that the intrinsic in-plane resolution limit for PET can be improved by simply acquiring PET images in the presence of a magnetic field where the field lines are normal to the image in the plane. This is the condition that is depicted in FIG. 1.

In combining a PET scanner with an NMR scanner the rather substantial fields required for positron confinement are already available from the substantial magnetic field generated by the magnetic imaging structure of the NMR device and particularly superconducting magnet 2. In addition, the same computer employed for NMR imaging may be utilized with appropriate algorithms to produce PET images. For example, if the range of a 0.959 MeV positron in tissue is considered, the positron range will be 3.91 mm in the absence of a magnetic field. In the presence of a 5.0 T magnetic field, the positron range will vary form 3.91 mm for a trajectory parallel to the field lines to 0.91 mm for a trajectory normal to the field lines, based on the first-order approximation noted above.

Figure 6:
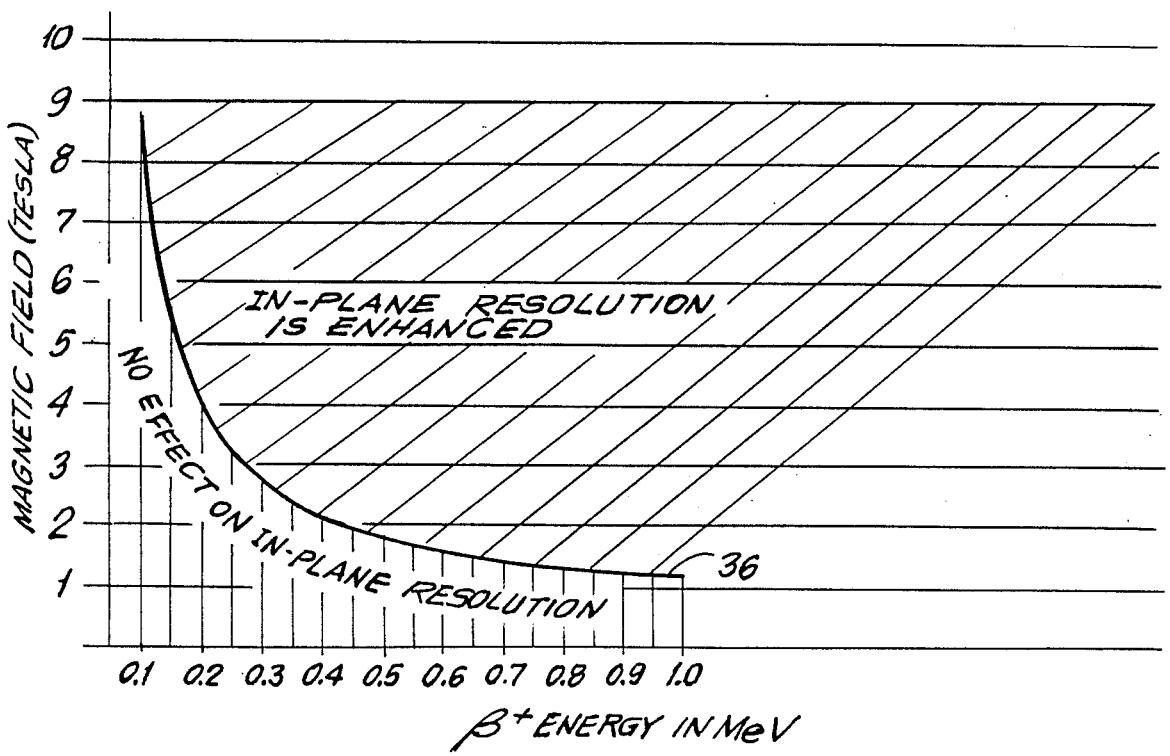
FIG. 6 is a diagram graphically illustrating the relationship between magnetic field and positron energy in increasing the in-plane resolution of a PET image wherein positron energy in MeV is plotted along the abscissa and the magnetic field strength in Tesla units is plotted along the ordinate.

FIG. 6 is a diagram graphically illustrating the relationship between magnetic field and positron energy in increasing the in-plane resolution of a PET image wherein positron energy in MeV is plotted along the abscissa and the magnetic field strength in Tesla units is plotted along the ordinate. FIG. 6 illustrates that a combination of small magnetic field strengths and low positron energies do not improve in-plane resolution. However, with more energetic positrons and stronger magnetic field strengths, enhanced in-plane resolution results. Thus, the entire area above the curve 36 corresponds to an area where in-plane resolution is improved by the presence of a transversely disposed magnetic field with respect to $\beta+$ trajectory.

Figure 7:
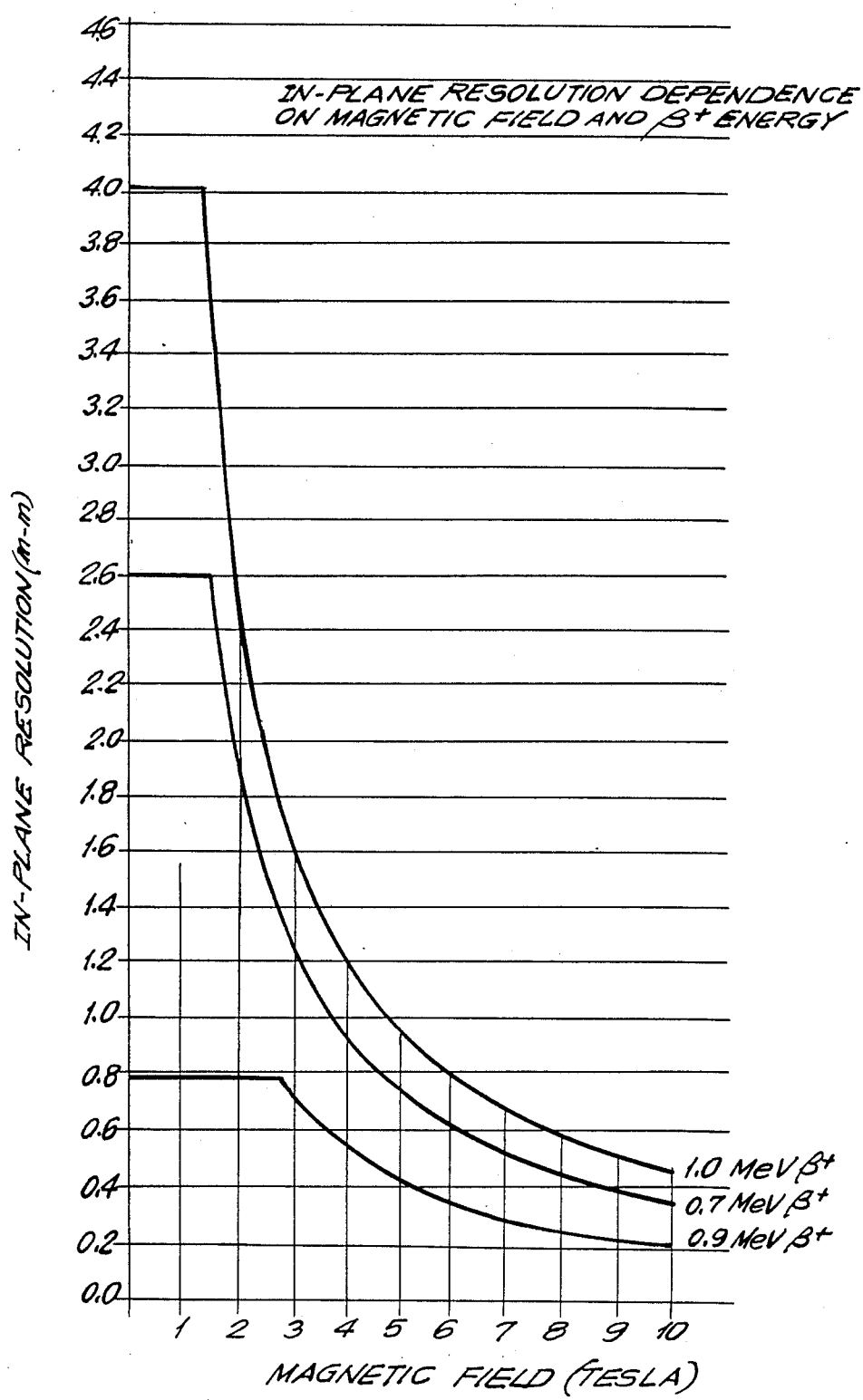
FIG. 7 is a diagram illustrating the in-plane resolution dependence on magnetic field and positron energy wherein magnetic field in Tesla units is plotted along the abscissa and in-plane resolution in millimeters is plotted along the ordinate.

Similarly, FIG. 7 is a diagram graphically illustrating the in-plane resolution dependence on magnetic field and positron energy wherein magnetic field in Tesla units is plotted along the abscissa while in-plane resolution in millimeters is plotted along the ordinate. As readily indicated in FIG. 7, if in-plane resolution is examined as a function of magnetic field, at a number of positron energies, a family of curves are generated. In FIG. 7, curves for 1, 0.7, and 0.3 MeV have been plotted. At lower field strengths a plateau is seen for each curve. The plateau occurs when a magnetic field is too weak to produce and/or the rate is less than the linear range of a positron in tissue. However, with magnetic field strengths above this level and within a range clearly available from NMR imaging systems, a substantial improvement in in-plane resolution occurs.

The NMR/PET scanner apparatus according to the instant invention clearly yields apparatus which is significantly more powerful than its separate components. The data acquired by NMR and PET techniques is complimentary while the in-plane resolution for PET imaging is enhanced by the tranverse magnetic field readily available from the NMR imaging structure. Further, the same computer, employing different algorithms, may be employed for the creation of images in each case so that clearly a more cost effective combination results.

While the invention herein has been disclosed in regard to a rather specific embodiment thereof, it will be apparent to those with ordinary skill in the art that the teachings herein and the apparatus set forth may be varied to suit specific design preferences or operational needs and may well be varied as a function of the individual nature of the research or diagnostics to be perfomed. For example, alternate forms of scintillation crystals, and devices for coupling light flashes resulting from photon detection therein to a photodetector disposed away from or insensitive to the magnetic field associated with the NMR imaging system may be readily employed. Thus, fiber optics may be utilized to replace the right angle quartz prism and light pipe and alternate forms of photodetector devices such as photodiodes may be utilized. Furthermore, the scintillation crystals may be varied to suit choice of design and such choice of design may include any of the crystals noted above, or the like or the same may be replaced by superconducting colloidal detectors. Here ionizing particle interaction with these devices causes a change in magnetic flux in the unit than a production of light. A pick-up coil or the like can be employed to sense such changes in flux.

Thus, although the instant invention has been described in connection with a highly specific exemplary embodiment thereof, it will be understood that many modifications and variations thereof will be readitly apparent to those of ordinary skill in the art. Therefore, it is manifestly intended that this invention be only limited by the claims and the equivalents thereof.

What is claimed is:

1. NMR-PET scanner apparatus comprising:
    means for establishing a substantially uniform magnetic field in a first direction through a defined volume;
    scintillation means disposed in said defined volume in a plane which is at least partially transverse to said first direction;
    photodetector means disposed at a location removed from said defined volume to reduce interaction with said uniform magnetic field; and
    means for establishing light communication between said scintillation means and said photodetector means to enable light pulses generated by said scintillation means to be transduced into electrical signals by said photodetector means.

2. The NMR-PET scanner apparatus according to claim 1 wherein said scintillation means takes the form of a plurality of individual scintillation crystals arrayed in a closed, planar geometric form.

3. The NMR-PET scanner apparatus according to claim 2 wherein said photodetector means comprises a plurality of individual photodetectors, each of said plurality of individual photodetectors being associated with one of said plurality of individual scintillation crystals and in light communication therewith.

4. The NMR-PET scanner apparatus according to claim 3 wherein said means for establishing light communication between said scintillation means and said photodetector means comprises a plurality of non-conductive, non-magnetic light transmitting elements, each of said plurality of light transmitting elements being disposed intermediate respective ones of said plurality of individual scintillation crystals and said plurality of individual photodetectors.

5. The NMR-PET scanner apparatus according to claim 4 wherein each of said plurality of non-conductive, non-magnetic light transmitting elements takes the form of a light pipe.

6. The NMR-PET scanner apparatus according to claim 5 wherein each light pipe takes the form of an acrylic cast rod.

7. The NMR-PET scanner apparatus according to claim 5 wherein said defined volume is cylindrical and said first direction is in an axial direction of said cylindrical volume.

8. The NMR-PET scanner apparatus according to claim 5 wherein said closed, planar geometric form is a ring and said plurality of individual scintillation crystals are arranged in said ring.

9. The NMR-PET scanner apparatus according to claim 8 wherein each light pipe is interfaced to an associated one of said plurality of individual scintillation crystals in said ring through a right angle quartz prism.

10. The NMR-PET scanner apparatus according to claim 9 wherein each of said plurality of individual photodetectors takes the form of a shielded photomultiplier tube connected to a respective one of said light pipes at an end thereof opposite to said right angle quartz prism.

11. The NMR-PET scanner apparatus according to claim 10 wherein said means for establishing a substantially uniform magnetic field takes the form of a superconducting magnetic stucture.

12. The NMR-PET scanner apparatus according to claim 11 wherein each of said individual scintillation crystals takes the form of a sodium iodide (NaI(Tl)) crystal.

* * * * *